(12) United States Patent
Quong

(10) Patent No.: US 6,562,361 B2
(45) Date of Patent: May 13, 2003

(54) PHEROMONE IMMOBILIZED IN STABLE HYDROGEL MICROBEADS

(75) Inventor: Douglas Quong, London (CA)

(73) Assignee: 3M Innovative Properties Company, St. Paul, MN (US)

( * ) Notice: Subject to any disclaimer, the term of this patent is extended or adjusted under 35 U.S.C. 154(b) by 15 days.

(21) Appl. No.: 09/847,464

(22) Filed: May 2, 2001

(65) Prior Publication Data

US 2002/0164364 A1 Nov. 7, 2002

(51) Int. Cl.$^7$ .................. A01M 25/00; A61K 9/14; A61K 9/50
(52) U.S. Cl. ................ 424/408; 424/84; 424/450; 424/488; 424/407; 424/404; 424/405; 424/489; 424/486; 424/487
(58) Field of Search .................. 424/408, 404, 424/405, 407, 451, 455, 456, 489, 488, 499, 500, 493, 400; 514/962

(56) References Cited

U.S. PATENT DOCUMENTS

| | | | |
|---|---|---|---|
| 2,800,457 A | * 7/1957 | Green et al. | 252/316 |
| 3,577,515 A | 5/1971 | Vandegaer | 424/32 |
| 3,687,865 A | 8/1972 | Katayama et al. | 252/316 |
| 3,691,140 A | 9/1972 | Silver | 260/78.5 |
| 3,956,172 A | 5/1976 | Saeki et al. | 252/316 |
| 4,285,720 A | 8/1981 | Scher | 71/88 |
| 4,325,941 A | 4/1982 | Dal Moro et al. | 424/84 |
| 4,400,391 A | * 8/1983 | Connick, Jr. | 424/304 |
| 4,402,856 A | 9/1983 | Schnoring et al. | 428/402.22 |
| 4,436,719 A | 3/1984 | Lindaberry | 424/37 |
| 4,487,759 A | 12/1984 | Nesbitt et al. | 424/32 |
| 4,532,123 A | * 7/1985 | Gardner | 424/21 |
| 4,670,250 A | 6/1987 | Baker | 424/419 |
| 4,689,293 A | 8/1987 | Goosen et al. | 435/1 |
| 4,755,377 A | 7/1988 | Steer | 424/76.4 |
| 4,911,928 A | 3/1990 | Wallach | 424/450 |
| 5,023,024 A | 6/1991 | Kyogoku et al. | 264/4.3 |
| 5,045,569 A | 9/1991 | Delgado | 521/60 |
| 5,051,304 A | 9/1991 | David et al. | 428/402.2 |
| 5,508,313 A | 4/1996 | Delgado et al. | 521/63 |
| 5,603,952 A | 2/1997 | Soper | 424/456 |
| 5,645,844 A | 7/1997 | Henderson et al. | 424/405 |
| 6,039,901 A | 3/2000 | Soper et al. | 264/4.3 |
| 6,080,418 A | * 6/2000 | Sengupta et al. | 424/408 |
| 6,365,189 B1 | * 4/2002 | Quong | 424/489 |
| 6,375,968 B1 | * 4/2002 | Quong | 424/408 |

FOREIGN PATENT DOCUMENTS

| | | | |
|---|---|---|---|
| DE | 30 32 616 | 3/1981 | |
| EP | 0 371635 | 6/1990 | ......... C08F/220/18 |
| GB | 1236855 | 6/1971 | |
| JP | 60 048923 | 3/1985 | |
| JP | 05 238957 | 9/1993 | |
| JP | 8-173794 | 7/1996 | ............ B01J/13/02 |
| WO | 95/14379 | 6/1995 | .......... A01N/25/10 |
| WO | WO 98 45036 | 10/1998 | |
| WO | 00/05446 | 2/2000 | .......... D06M/23/12 |
| WO | WO 00/48465 A1 | * 8/2000 | |
| WO | WO 01 30146 | 5/2001 | |

OTHER PUBLICATIONS

Database CA 'Online, Chemical Abstract Service, Columbus, Ohio, US; S. Omi et al. "Microencapsulation of pherome analogs and measurement of the sustained release", retrieved from STN–International, Database accession No. 116:2284, XP002212606 abstract & J. Microencapsulation, vol. 8, No. 4, 1991, pp. 465–478.

Siddiqui et al., "Physical Factors Affecting Microencapsulation by Simple Coarcervation of Gelatin", *J. Pharm. Pharmacol.*, pp. 70–73 (1983).

Peters, et al., "Effect of Gelatin Properties in Complex Coacervation Processes", *Drug Development and Industrial Pharmacy*, 18(1), pp. 123–134 (1992).

Akin, et al., "Crontrolled Release of a Herbicide From Crosslinked Gelatin Micropheres", *Minutes Int. Symp. Microencapsulation*, $9^{th}$ pp. 191–194 (1994).

Rabiskova et al., "The Influence of HLB on the Encapsulation of Oils by Complex Coacervation", *J. Microencapsulation*, vol. 15, No. 6, pp. 747–751 (1998).

* cited by examiner

*Primary Examiner*—Thurman K. Page
*Assistant Examiner*—Rachel M. Bennett
(74) *Attorney, Agent, or Firm*—Dale A. Bjorkman

(57) ABSTRACT

A microbead comprising pheromone encapsulated in a coacervate shell is provided. The coacervate shell is entrained in a hydrogel microbead without chemical crosslinking. The microbeads of the present invention are capable of dehydration and rehydration to release of pheromone to the intended environment.

16 Claims, No Drawings

PHEROMONE IMMOBILIZED IN STABLE HYDROGEL MICROBEADS

FIELD OF THE INVENTION

The invention relates broadly to a combination of encapsulation, immobilization and release of active material using hydrogel microbeads. Specifically, the active material is encapsulated in a coacervate shell and immobilized in a hydrophilic microbead.

BACKGROUND

Methods of eliminating unwanted pests from orchards, crops and forests frequently entail the use of organophosphate insecticides. Alternative methods involve insect mating disruption, where insect pheromones are used to control pests and protect agricultural crop. In insect mating disruption methods, the mating pheromone plume of a female insect is typically masked with other pheromone point sources. This reduces the likelihood of a male insect finding a female, and subsequently disrupts and reduces larvae production. The insect population of the next generation is thus decreased, as well as potential crop damage.

Conventional sprayable pheromone formulations are generally provided in liquid filled microcapsules containing an active. Typically, the microcapsules have a polyurea shell that can be formed using an interfacial process involving an isocyanate and an amine. Microencapsulation by this method has been descibed for example in U.S. Pat. No. 4,487,759 (Nesbitt et al.) These polyurea shells allow actives to be released into the atmosphere for up to a total of 2–3 weeks for most insect pheromones. Shells of polyurea capsules are generally semi-permeable, therefore active material can diffuse across the shells and release slowly with time. Potentially, high concentrations of active in the air can be observed immediately upon delivery or spraying of encapsulated products. This may be attributable to a high occurrence of capsule bursts or potential leaks in microcapsules.

U.S. Pat. No. 4,532,123 (Gardner) teaches capsules containing a pharmaceutical active material in primary capsules, that are further encapsulated within a second shell to create secondary capsules. The intracapsular liquid core of the secondary capsules contain enzymes which slowly hydrolyze the shell of the primary capsules. This slow hydrolysis enables the slow release of active from the primary capsules into the larger capsular core for controlled delivery.

A Japanese patent, JP 8-173794 teaches encapsulation of an amine within small capsules of polymethyl methacrylate shells. These capsules are further encapsulated within an epoxy-amine polymeric shell. Similarly, the amine within the tiny capsules is released into the core of the larger capsule ultimately delivering the amine upon rupturing of the polymeric shells.

Use of interfacial condensation to encapsulate substances such as pharmaceuticals, pesticides and herbicides is taught in U.S. Pat. No. 3,577,515 (Vandegaer). The encapsulation process involves two immiscible liquid phases (typically water and an organic solvent), one being dispersed in the other by agitation, and the subsequent polymerization of monomers from each phase at the interface between the bulk (continuous) phase, and the dispersed droplets. Polyurethanes and polyureas are materials suitable for producing the microcapsules. The microcapsules comprising a polymeric sphere and a liquid centre, ranging from 30 micron to 2 mm in diameter, depending on monomers and solvents used.

Highly viscous and thickened hydrogels have been used to deliver pheromones, fragrances and other non-water soluble actives. U.S. Pat. No. 4,755,377 (Steer) describes a process of encapsulating perfume or fragrant material within an aqueous-based gel composition. The resulting material is in the form of a highly viscous semi-solid. U.S. Pat. No. 5,645,844 (Henderson et al.) describes the use of chitosan paste for delivery of pheromones to disrupt insect mating, where the material can be dispensed by an apparatus such as a caulking gun. Due to their thickness and high viscosity, these materials, however, are generally unsprayable compositions.

Most hydrogels are safe and non-toxic to humans. Hydrogels have been used for the encapsulation of biological materials whereby the formulation is non-lethal to the viability of the cells, proteins, and related materials. U.S. Pat. No. 4,689,293 (Goosen et al.) describes the process of encapsulating living tissue or cells. The encapsulation shell permits the passage of materials and oxygen to the cells and permits the diffusion of the metabolic by-products from the gel.

Coacervation process is well known in the art for uses such as carbonless copy paper capsules and in encapsulation of leuco dyes, drugs, flavorings and fragrances. U.S. Pat. No. 2,800,457 (Green) discloses a gelled colloid that is porous and that the pores may be tightened if the crosslinking step is conducted at pH of 9–10.

Other approaches to crosslinking a coacervate microcapsule have employed non-aldehyde crosslinkers. U.S. Pat. No. 4,402,856 (Schnoring) discloses the use of a natural and/or synthetic tanning agent and a carbonyl compound to harden a gelatin microcapsule. U.S. Pat. No. 5,023,024 (Kyogoku et al.) discloses the use of naturally occurring chemicals of the iridoid class, specifically genipin. U.S. Pat. No. 5,051,304 (David et al.) also discloses the use of tannic acid as a crosslinker.

Although the foregoing approaches have proved satisfactory for crosslinking a coacervate shell under certain conditions, the need still exists to provide coacervate shells that are more environmentally friendly, do not utilize toxic crosslinkers, and are more cost effective than previously disclosed.

SUMMARY OF THE INVENTION

The present invention provides a method of encapsulating a pheromone comprising:

a) providing a solution comprising a first polymer capable of forming a microcapsule by complex coacervation; a pheromone; and a second polymer, said second polymer being capable of forming a microcapsule by complex coacervation with the composition comprising the first polymer;

b) establishing a microcapsule having a coacervation shell without chemical crosslinking of said shell;

c) adding a third polymer, said third polymer being suitable to form a hydrogel microbead, in an amount effective to form the microcapsule containing composition; and d) spraying the microcapsule containing composition into a coordination solution, thereby providing stable hydrogel microbeads comprising microcapsules having a coacervation shell without chemical crosslinking.

Another aspect of the present invention is a method of encapsulating a pheromone wherein the third polymer of step c) above is added before the microcapsule of step b) is established.

The present invention also provides a pheromone that is encapsulated in a coacervate shell by the above named process.

The hydrogel microbead is preferably hydrophilic and is capable of immobilizing a broad spectrum of microencapsulated active materials, either water-soluble or non-water soluble.

In an aspect of the invention, the hydrogel microbead may be made from a water-soluble microcapsule containing material to provide an environmentally friendly microbead. The microbeads may be coated with an adhesive to improve application in an intended environment.

In a further aspect of the invention, the microbeads may be capable of re-hydrating after an initial dehydration and release of active. Thus, the release and longevity of the pheromone can be controlled by adjusting the humidity of the environment in which the microbeads have been delivered.

DETAILED DESCRIPTION OF THE PREFERRED EMBODIMENTS

The present invention provides a pheromone encapsulated within a coacervate shell which in turn is entrained within a hydrogel microbead without an intermediate step of chemically crosslinking the coacervate shell. For purposes of the present invention, a chemical crosslink is a crosslink between two polymers formed by covalent bonds. Thus, the present invention provides effective delivery of pheromones from a hydrogel microbead structure without the use of potentially environmentally unfriendly chemicals, thus avoiding the use of chemicals such as glutaraldehyde, formaldehyde, and tannic acid, among others. The present invention additionally reduces the incidence of premature release of the pheromones from the microcapsules. The present invention also delays and/or prolongs the release of pheromones from the coacervate shell as compared to coacervate shell-formed microcapsules that are not entrained within a hydrogel microbead. Uncrosslinked coacervate microcapsules that are not entrained within a hydrogel microbead are typically unstable. By "unstable" is meant that the coacervate microcapsule lacks form or shape to encapsulate the pheromone, thereby rendering it unfit for the purpose of delivering the pheromone material to the intended environment.

In view of the increasing awareness of insecticide toxicity to humans and other environmental concerns, it would be advantageous to provide a pheromone delivery system having an extended release life, as well as having both an encapsulated shell and a hydrogel microbead that is non-toxic and biodegradable. It would also be advantageous to provide a system for sprayable, long-lasting pheromone delivery that would be applicable to a broad spectrum of pheromone material thereby eliminating the issue of reactivity of the pheromone with one or more of the shell components.

The method of the invention can be used to encapsulate pheromones with functional groups such as acetates, aldehydes, ketones, alcohols, esters, epoxies, ethers, or combinations thereof. Pheromones may be defined as compounds which, when naturally produced, are secreted by one member of an animal species which can influence the behavior or development of another member of the same animal species. Pheromones are species-specific and therefore the application of pheromones for insect behavior modification has minimal effect on non-target pests. Pheromones supplied for modification of insect behavior interfere with the "mate finding process" by releasing point sources of pheromone, which may compete with or camouflage the pheromone plume of a female. This latter type of action differs from chemical insecticides or insect growth regulators or hormones, in that pheromones target future generations of insects, not present ones. As pheromones are very species-specific and are used only in small quantities, their use is more environmentally acceptable than broadcasting of pesticides.

Many pheromones have an ester terminal group, for example and acetate or formate group. Typically these substances are water-immiscible and incorporation of them into microcapsules by known methods presents no particular problem. Additional pheromones that can be encapsulated and then immobilized within the hydrogel microbeads include aldehydes, esters, alcohols, epoxy compounds, ethers, ketones, or combinations thereof. This invention is particularly advantageous for delivery of pheromones containing reactive ketones in which the double bond of the carbonyl group is conjugated with one or more double bonds, for example acetophenone where the carbonyl group is conjugated with double bonds of the aromatic ring.

Pheromones useful in the invention are preferably insect pheromones. In describing the structure of the a pheromone, the following notation is used: the type (E (trans) or Z(cis)) and position of the double bond or bonds are given first, the number of carbon atoms in the chain is given next and the nature of the end group is given last. To illustrate, the pheromone Z-10 C19 aldehyde has the structure;

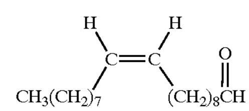

Pheromones can be mixtures of compounds with one component of the mixture predominating, or at least being a significant component. Partially water-miscible significant or predominant components of insect pheromones, with the target species in brackets, include, for example: E/Z-11 C14 aldehyde (Eastern Spruce Budworm), Z-10 C19 aldehyde (Yellow Headed Spruce Sawfly), Z-11 C14 alcohol (Oblique Banded Leafroller), Z-8 C12 alcohol (Oriental Fruit moth), E,E-8,10 C12 alcohol (Codling moth), E-11 C14 alcohol (Tufted Apple Budmoth), E-11 C14 acetate (Sparganothis Fruitworm), Z-11 C14 acetate (Blackheaded Fireworm), Z-9 C12 acetate (Grape Berry Moth), Z-11 C14 acetate (Leafroller), E/Z-4 C 13 acetate (Tomato Pinworm), Z,Z/Z,E-7, 11-C 16 acetate (Gossyplure), Z-8-C12 acetate (Oriental Fruit Moth), Z/Z-3,13 C18 acetate (Peach Tree Borer), E,Z/Z,Z-3,13-C18 acetate (Lesser Peach Tree Borer), and 7,8-Epoxy-2-methyl-C18 (Gypsy Moth), among others.

An example of a ketone that is a pheromone is E or Z 7-tetradecen-2-one, which is effective with the oriental beetle. An ether that is not a pheromone but is of value is 4-allylanisole, which can be used to render pine trees unattractive to the Southern pine beetle.

Other compounds may optionally be included in the microcapsules of the invention, including perfumes, fragrances, flavoring agents, co-attractants and the like.

Optionally, oil absorbents can be incorporated into the pheromone droplets. These absorbents can help retain the pheromone droplets within the microcapsules, resulting in longer lasting formulations. Clays and starches could alternatively be used for this purpose.

The concentration of pheromone in the microcapsules of the invention should be at a level such that the hydrogel microbead can still provide a strong, rupture resistant network and deliver an effective amount of the pheromone to the environment to which it is intended. Thus, the pheromone is preferably present in an amount between about 0.1 wt % to about 60 wt % (weight percent) of the total weight of the microbead. More preferably, the amount of pheromone is present in the microbead at between about 0.2 wt % to about 40 wt %; and most preferably between about 0.3 wt % to about 20 wt %.

The present invention relates in part to encapsulation of pheromones within a coacervate microcapsule or shell. Conventional coacervate shells utilize crosslinkers to harden the shell encapsulating the pheromone material. The coacervate shell of the present invention is stable without the use of potentially toxic or undesirable crosslinking agents, such as aldehydes, ketones or acids. Uncrosslinked coacervate microcapsules that are not entrained within a hydrogel microbead are typically unstable. Typical crosslinking agents have toxic effects or are deemed less environmentally friendly. An advantage of the present invention is the ability to avoid use of potentially toxic or undesirable chemical crosslinkers.

Coacervate shells are typically formed by the phase separation resulting from the neutralization of two oppositely charged colloids. Typical colloids usable to form a coacervate shell of the present invention include a cationic polymer and an anionic polymer. Cationic polymers usable for coacervation include gelatin, chitosan, poly (hexamethylene co-guanidine), and poly-L-lysine, among others. Anionic polymers include gum arabic, gum acacia, alginates, carboxymethyl cellulose, ethylene maleic anhydride (EMA), gelatins, carrageenan, poly(acrylic acid), pectin, serum albumin, starch, and polyphosphates, and the like. Preferably, the coacervate shell of the present invention comprises a gelatin and an alginate or gum arabic, or combinations thereof.

The present invention further involves immobilizing a coacervate shell that encapsulates a pheromone within a hydrogel microbead. This immobilization thus provides encapsulated pheromone in a protective microbead format. The microbeads can be suspended in a solution to provide a delivery system for pheromones, where the system is capable of providing extended release periods. The microbead provides physical protection to the microcapsules from external pressures such as those that can occur during a spray delivery, for example. This in turn minimizes premature capsule bursts (rupturing) and prolongs the release period of the pheromone(s). Upon dehydration of the water from the hydrophilic microbead, the microcapsule containing the pheromone remains immobilized within the microbead. The pheromone is able to then release into the desired environment by diffusion through the capsule shell, followed by diffusion past or through the hydrophilic microbead.

Microcapsules having a coacervation shell without chemical crosslinking of the shell are established through a conventional complex coacervation process. In this process, a first polymer and a second polymer capable of forming a coacervation shell with the first polymer are mixed. In this process, the two polymers form a coacervate in response to a change in their environment, such as pH, temperature, dilution, and the like. Typically, the first and second polymer solutions each possess a respective charge. The "charge" as used herein relates to the functionality of the polymer such that when the encapsulation composition containing the polymers and the pheromone is adjusted by pH or other environmental manipulations, the polymers interact such that they establish a microcapsule having a coacervation shell without chemical crosslinking of the shell. The procedure of coacervation is within the purview of one skilled in the art.

The composition of cationic and anionic polymers are preferably then caused to form a complex by dilution. In some instances, the pH of the composition may need to be adjusted. Prior to adjusting pH or other environmental conditions, the composition may be mixed such that droplets of pheromone are distributed within an aqueous continuous phase to allow the coacervate shell to form around the droplets, thereby forming relatively uniform, round, or elliptical microcapsules containing pheromone. This dilution and/or pH adjustment causes a gel to be formed around the oil soluble pheromones as the temperatures are lowered to below the gel point of the composition.

The hydrogel microbead of the present invention typically entrains the coacervate microcapsules described above. The microbeads of the present invention may comprise a microcapsule-containing material and pheromone. The hydrogel microbead is also preferably hydrophilic. The degree and extent of agitation as well as the type of surfactant used to form the microbeads can affect the size and the dispersity of microcapsules within the microbead. Microcapsules entrained within the microbead are preferably between about 0.01 nm to about 300,000 nm in diameter. More preferably, the microcapsules are between about 0.5 nm to about 200,000 nm in diameter.

Microcapsule-containing materials useful in the present invention for making the hydrogel microbead are biocompatible, water-soluble, have pendant functional groups, and complex with ions (e.g., polyvalent cations and/or anions) to form hydrogels. Functional groups of the microcapsule-containing material include for example, carboxyls, hydroxyls, primary or secondary amines, aldehydes, ketones, esters, and combinations thereof. Preferably the hydrophilic microcapsule-containing material can be made from naturally occuring polysaccharides, such as alginates, chitosans, gums, agars, carrageenans, or the matrix can be made synthetic, water soluble monomers, oligomers or polymers, such as, for example, polyvinyl alcohol, poly(N-isoproylacrylamide), acrylamides, acrylates, and methacrylates, or combinations thereof.

Suitable naturally occurring polysaccharides include the water-soluble salts of alginic, pectic and hyaluronic acids, the water-soluble salts or esters of polyglucuronic acid, polymanuronic acid, polylygalacturonic acid and polyarabinic acid, and gum kappa-carrageenan. The preferred polysaccharides are the ammonium, magnesium, potassium, sodium and other alkali metal salts of alginic acid, and the most preferred polysaccharide is sodium alginate.

"Alginate" is the general name given to alginic acid and its salts. Alginates are composed of D-mannosyluronic (mannuronic-"M") and L-gulopyranosyluronic (guluronic-"G") acid residues. The alginate used to immoblize pheromone droplets should be carefully selected to ensure proper microbead formation, ensure the stability of the microbeads during storage and delivery applications, and ensure that the microbeads are able to shrink and swell appropriately to deliver the desired pheromone over an extended period of time (preferably 4–6 weeks). Preferably, an alginate is chosen such that the microbead formed is sufficient in strength to withstand the shear forces (conditions) placed upon the microbeads during application via a spray nozzle- i.e., the microbeads are resistant to rupture during the spray application.

For strength and stability of the microbeads, it is desirable to choose the molecular weight and M:G ratio of the alginate to obtain preferred properties of the ultimate microbead. Although alginates high in mannuronic acid are generally useful for thickening applications, whereas alginates with a high level of guluronic acid are often used for forming gels, both alginate categories (individually or a mixture thereof) are suitable for the microbeads of the invention. A preferred alginate that imparts strength and rupture resistance is an alginate that has a high level of guluronic acid, e.g., greater than about 30 percent by weight. Alginate compositions with excessive levels of mannuronic acid could result in less stable and less rigid microbeads than high guluronic acid gels. However, high mannuronic acid alginates impart to the microbeads the capability of swelling and absorbing more water than microbeads of high guluronic acid content. Thus, a careful balance of the advantages imparted by each of M and G residues should be considered when choosing a suitable alginate.

Preferably, alginates used in the microbeads of the invention have a molecular weight in the range of about 100,000 to about 2,500,000, more preferably about 200,000 to about 1,500,000. Furthermore, the alginates preferably have an M:G ratio in the range of about 0.2 to about 3.5; more preferably about 0.3 to about 1.85.

Preferred alginates have a high level of guluronic acid, for example are alginates from the algae *Laminaria hyperborea*, stem, whole plant or frond. Preferred alginates with high levels of mannuronic acid include *Ascophyllum nodosum*, for example.

Gel matrices that form the hydrogel microbead of the present invention may be formed, for example, by coordinating polysaccharides bearing pendant carboxylate groups. These polysaccharide compounds are composed of water-insoluble alginates which include, with the exception of magnesium and the alkali metal salts, the group II metal salts of alginic acid. The water-insoluble alginate gels are typically formed by the chemical conversion of water-soluble alginates, in an aqueous solution, into water-insoluble alginates. This conversion usually is accomplished by the reaction of a water-soluble alginate with polyvalent cations released from a soluble di- or trivalent metal salt.

Water-soluble alginates can include the ammonium, magnesium, potassium, sodium, and other alkali metal salts of alginic acid. Water-insoluble di-or trivalent metal salts suitable for the present invention should satisfy two requirements: (1) that the water-insoluble metal salt contain a di-or trivalent metal ion capable of complexing with the pendant carboxylate groups of the water-soluble polysaccharide to cause the formation of a water-insoluble polysaccharide gel; and (2) that the water-insoluble metal salt reacts with a water-soluble acid to form a water-soluble metal salt.

A common and suitable alginate gel is composed of calcium aliginate.

The time of gelation of the calcium alginate gels can be accomplished by regulating the concentration of free calcium ions in the solution. Typically, the concentration of free calcium ions is controlled by manipulation of the ionization rate of the calcium salt and/or by the inclusion of other compounds in the solution which react with the free calcium ions.

The process of making the microbeads of the invention preferably comprises making the pheromone-filled microcapsules and dispersing the microcapsule suspension in the hydrophilic microcapsule-containing material. The mixture is then hardened (gelled) to form microbeads. The resulting microbead is a hydrogel microbead, having greater than about 30% water initially. The pheromone-filled microcapsules are dispersed and entrained within the water-polymer microbead.

The hydrophilic microbead with the microcapsules entrained in the microbead can be formed either by ionic interactions or by thermal setting. When forming microbeads by ionic interactions, there are two preferred methods of forming: (1) the spray method and (2) the emusification method. In the spray method, the microcapsule-containing mixture is mixed and then atomized mechanically to form small spherical droplets. The size of the microbeads is generally governed by the intrinsic properties of the emulsion suspension, the feed rate and the coaxial airflow rate.

The droplets which are atomized can then be allowed to free-fall directly into a reacting bath. The reacting bath cures or sets the hydrogels so that they solidify. Reaction bath curing can be achieved through chemical or non-chemical means. For the case of sodium alginates, calcium ions are used to coordinate the polymer chains. A preferred coordination compound is calcium chloride.

For the purpose of the present invention, "coordination compounds" relates to chemicals or compounds that are usable to give the hydrogel microbead and the coacervate shell structure such that it can be applied to its intended environment. Suitable coordinating compounds are preferably divalent and multivalent ionic compounds, such as low molecular weight inorganic or organic compounds including monomers, oligomers and polymers. An example of a suitable coordination compound is Calcium (Ca++) ions for an alginate.

Sources for the coordination compound calcium ions used in the formation of alginate gels include, for example, calcium carbonate, calcium sulfate, calcium chloride, calcium phosphate, calcium tartrate, calcium nitrate, and calcium hydroxide. Other acceptable coordination compounds may include lanthanum chloride, ferric chloride, cobaltous chloride, as generally are other compounds with multivalent cations, such as calcium (Ca++), copper (Cu++), barium (Ba++), strontium (Sr++) and the like.

Alternatively, an emulsification method can be used to produce hydrogel microbeads. In selecting the continuous phase material, it is preferable that it be immiscible with the aqueous microcapsule-containing material.

The microcapsule-containing material preferably has a range of concentrations usable in practicing the invention. The concentration should be chosen to optimize ease of handling, gelling time, the strength of the hydrogel microbead around the pheromone droplets. For example, a sodium alginate solution can preferably be prepared in a concentration of about 1 to about 10% (w/v) in water, more preferably about 1.5 to about 5% and most preferably from about 1 to 3%. However, if the hydrogel agent concentration is too high, the solution may be so viscous as to hinder the formation of spherical microbeads.

Alternatively, hydrogel microbeads of the invention can be formed, for example, by adding the microcapsule-containing material solution drop-wise to a selected coordination compound. For example, a method can be used whereby droplet formation and coordination compound addition is completed as a one step process by a vibrating nozzle which ejects a hydrogel droplet from one source and coats the droplet with a coordination compound from another. U.S. Pat. No. 4,701,326 teaches use of this method.

In the preferred aspect where alginates are used to immobilize an pheromone, a coordinating solution is preferably made up at a concentration of 1 to 1000 millimolar, more preferably 20 to 500 millimolar and most preferably from 50 to 100 millimolar. The concentration ranges may have to be adjusted, depending on the nature of a coordination compound and microcapsule-containing material.

The microcapsule-containing material and pheromone can be treated with the coordination compound or solution by soaking, spraying, dipping, pouring or any of sever other methods which will deposit an amount of the complexing agent on the droplet. When soaking, the time in solution may be from 1 second to 24 hours, preferably 1 minute to 1 hour, and more preferably from 10 to 30 minutes.

The temperature for hydrogel microbead formation is preferably chosen as to avoid damage or alteration to the pheromone. For example, in the preferred aspect where alginates are utilized, the temperature is preferably in the range of about 1° C. to about 70° C.; more preferably between about 10° C. to about 40° C., and most preferably between about 15° C. to about 30° C.

To immobilize pheromone-filled microcapsules within a temperature setting, the microcapsule-containing material must first be solubilized in water using heat. The heating temperature is preferably be within a range of about 40° C. to about 100° C. When the microcapsule-containing material is completely dissolved, the temperature of the solution is lowered such that the solution is about 5° C. to about 10° C. above the gel setting temperature. A suspension containing pheromone-filled microcapsules is then preheated to a similar temperature to that of the microcapsule-containing solution, after which the two mixtures are blended together and mixed homogeneously.

To produce the microbeads, the molten microcapsule-containing material can be atomized through a nozzle system or be emulsified using an oil type continuous phase. In the spray method, the molten suspension can be atomized using coaxial air, for an example, and dropped into an ice bath containing distilled water. The microbead is then formed, entraining the microcapsules therein.

To produce the microbeads using the emulsification method, a continuous oil phase is preheated in a jacketed reactor to the temperature of the molten microcapsule suspension. The continuous phase may be any hydrophobic liquid. The preferred and most convenient liquid is a vegetable oil or mineral oil. Other possible hydrophobic liquids may include hydrofluorethers, siloxanes, or solvents such as cycloxhexanes and chloroforms. The microcapsule suspension is then emulsified in the continuous phase with the aid of a mixer. The mixing is continued until a desired particle size is obtained. The temperature of the reaction mixture is then lowered to that of ice water (about 5° C.). The matrix is then formed, entraining the microcapsules therein. The microbeads can then be filtered and washed prior to suspending them in solution for delivery.

The present invention provides microbeads having matrix cores that can provide sufficient immobilization of oil soluble pheromones and alcohol pheromones such that the pheromone can be delivered and sprayed by conventional techniques. The hydrophilic microbead preferably and advantageously imparts the capability of the hydrogel microbeads to immobilize the coacervate shell of oil-soluble and alcohol pheromones, and minimizes the risk of undesired reactivity between the pheromone and its immobilizer. Thus, immobilization of pheromones by use of the microbeads of the invention does not render the immobilized material inert or ineffective.

A further benefit from immobilizing pheromone in hydrogel microbeads is the ability of the hydrogel to "swell" under humid conditions and shrink under dry conditions. As used herein, "swell" is descriptive of the behavior of a microbead, wherein the size (volume) is enlarged (increased) due to absorption of water. This is likely due to the hydrophilic nature of the microcapsule-containing materials used to immobilize the pheromone.

In the presence of humidity, the hydrogel microbeads are preferably capable of absorbing moisture, rehydrating, and consequently releasing pheromone contained within the microbead. This behavior can be cyclical. Thus, by controlling the humidity (or dryness) of the ambient air, the release rate of pheromone from the microbeads can be controlled such that specific periods of release can be generally predicted. It is therefore possible with the present invention to release the pheromone on demand from the microbead. Release on demand, or "smart release," can be advantageous in those instances where release is preferred at certain times. The microbeads' ability to further release the pheromone may increase the longeveity of releasing effective amounts of the pheromone. Preferably, the microbeads are delivered to an intended environment in effective amounts to obtain the desired effect. For example, microbeads having pheromones entrained therein, are preferably delivered to a desired area in amounts such that mating disruption is effected and release is accomplished for more than 4 weeks, more preferably, the microbead can release for more than about 6 weeks; and most preferably more than about 8 weeks.

During the drying process (i.e dehydration) a surface film layer will form as a result of water evaporation from the hydrophilic microbead. Both initially and during use, the microbeads are characterized by a large surface area to volume ratio, which helps maintain the rate of diffusion of the pheromone during use. Thus, it has been found that microbeads made according to the method of present invention provide excellent delivery systems as they are capable of releasing the pheromone for extended periods. Furthermore, since the pheromone is dispersed within a water-based microbead, additional protection from environmental conditions (i.e., UV) can be provided.

Although it has been found that microbeads of the invention can be made having a diameter of up to about 5 millimeters (mm), it is preferred that the microbeads be between about 1 micrometer (elm) to about 1000 $\mu$m and more preferably between about 1 $\mu$m to about 500 $\mu$m in diameter to ensure that the microbeads are easily sprayable from conventional spray nozzles. Most preferably, to ensure minimal clogging in conventional nozzles, the microbeads are less than about 400 $\mu$m in diameter. It is conceivable, however, that with the advent of larger spray nozzles not currently used in the industry, the microbeads can be provided in much greater diameters.

For, spraying applications, particularly aerial spraying, it is desirable that the microbeads be capable of remaining suspended in solution (water) to ensure that the microbeads do not sink, settle, or coagulate in the suspension. This also ensures an even spray coverage. Preferably, the microbeads of the invention are able to remain in suspension, thus minimizing if not eliminating the need to agitate during application and optionally, during storage. Various suspension aids can also be included in the suspension containing the microbeads of the invention. Examples of suitable suspension aids include rhamsam gum, xanthum gum, gellan gum, gelatin, pectin, and gum arabic.

Owing to the handling to which the microbeads are subjected, it is desirable that the microbeads of the present invention should be somewhat elastic, and not frangible. For example, atomization of a suspension during a spray application may force the suspension through two rotating perforated discs that are immediately upstream of the discharge nozzle. Sufficient elasticity of the microbeads minimizes physical damage to the microbeads as they pass through the discs.

The microbeads of the present invention are preferably delivered in suspension in aqueous or solvent-based solutions. For environmental and biologically-friendly reasons, it is preferred that aqueous suspensions be used. Suspension aids are preferably included in the suspension formulations to ensure the microbeads remain suspended in solution.

Preferably, the suspension solution is substantially free of monovalent cations, such as sodium, to avoid degradation or breakdown of the microbeads. In a preferred aspect, a concentration of approximately 50 milliMolar of a coordination compound such as calcium chloride is maintained in a stored solution comprising the microbeads of the invention.

Optionally, adhesive material can be included in the compositions of the invention to assist in retention of the microbeads to an intended substrate. The adhesive material can be provided in various forms, such as for example, latex or a tacky microspheres. Adherent properties imparted to the hydrogel microbeads should result in the microbeads being able to still retain their suspended state and minimize aggregation or coagulation in the aqueous suspension. Furthermore, any adhesive material used to impart adherent properties should not affect the integrity of the particles; it should not dissolve or weaken the microbead(s).

A suitable adhesive material that may be included in the compositions of the invention is adhesive latex. The adhesive latex may be any suitable water-dispersible adhesive available in the art. In the agricultural business, such latex compositions are often called stickers or spreaders. Stickers are used to help non-encapsulated agriculture chemicals adhere to plants. Spreaders are used to help disperse non-encapsulated agriculture chemicals on application. Preferred adhesives are acrylate-based adhesives. One suitable latex is available from Rohm & Haas under the trade designation COMPANION. Another is available from Deerpoint Industries under the trade designation DPI S-100 (a proprietary sticker/spreader). Examples of such adhesives are polymers made from the "soft" monomers such as n-butyl acrylate, isooctyl acrylate, or the like, or copolymers made from a soft component, such as isobutylene, n-butyl acrylate, isooctyl acrylate, ethyl hexyl acrylate, or the like; and a polar monomer such as acrylic acid, acrylonitrile, acrylamide, methacrylic acid, methyl methacrylate or the like. Non-spherical polyacrylate adhesives are commercially available, for example, as the Rohm and Haas RHOPLEX line of adhesives. Preferably, the non-spherical polyacrylate adhesive is present in an amount of about 10–35% by weight of the total suspension.

Tacky microspheres of adhesive may alternatively be used to help adhere the hydrogel microbeads of the invention to an intended substrate. The tacky microspheres have sufficient adhesive properties to provide the desired adhesive function, yet there is no danger of completely coating the microbead which may lead to potentially inhibiting the release characteristics of the microbead. The combination of microbeads and tacky microspheres may be applied without the need to modify the orifices of conventional sprayers with minimal clogging or plugging problems. Furthermore, the incorporation of tacky (adhesive) microspheres to the (formulation) suspension of microbeads allows the microbeads' surfaces to become tacky. The beads can therefore stick to intended surfaces, such as, foliage and branches, for example. The adhesive microspheres, especially if they are hollow, may also absorb some of the pheromone into its own body, thus providing a second mechanism of release of the pheromone. This could result in an overall alteration, preferably an enhancement, of the release profile.

Preferably, the adhesive material is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569. Other suitable adhesives are the tacky microspheres having pendant hydrophilic polymeric or oligomeric moieties that are disclosed in U.S. Pat. No. 5,508,313.

Alternatively, the adhesive comprises between about 60–100% by weight of hollow, polymeric, acrylate, inherently tacky, infusible, solvent-insoluble, solvent-dispersible, elastomeric pressure-sensitive adhesive microspheres having a diameter of at least 1 micrometer, and between about 0–40% by weight of a non-spherical polyacrylate adhesive. The hollow microspheres are made in accordance with the teaching of European Patent Application 371,635.

Yet, another alternative is the association of certain type B gelatins with microencapsulated insecticides, especially those employing polyurea subunits in the microcapsule walls as disclosed in U.S. Pat. No. 4,436,719.

The compositions of the present invention may also include one or more adjuvants including, for example, gelling aids, preservatives, dyes, humectants, fixatives, emulsifiers, extenders, and freeze/thaw stabilizers such as polyhydric alcohols and their esters. These materials are present in an amount effective to achieve their extended function, generally less than about 5% typically less than 2%, by weight of the composition.

Incorporation of a light stabilizer can be included in the microbeads of the invention. Suitable light stabilizers include the tertiary phenylene diamine compounds disclosed in Canadian Patent No. 1,179,682, the disclosure of which is incorporated by reference. The light stabilizer can be incorporated by dissolving it, with the pheromone, in a water-immiscible solvent. Alternatively, a light stabilizer can be incorporated in the microbeads as taught in Canadian Patent No. 1,044,134, the disclosure of which is also incorporated by reference.

Surfactants may be used in the process of forming the microbeads. The incorporation of different surfactants will offer different types of microemulsion drop sizes of the pheromone within the hydrogel as well as dictate the amount of free oil lost in the reacting bath solution. A preferred surfactant has a high critical micelle concentration, such as for example, a product available under the product designation DISPONIL SUS IC 875 (CMC~1%), available from Henkel (Ambler, Pa.).

Particularly preferred surfactants are nonionic. Examples of suitable surfactants include polyvinylpyrrolidone (PVP) and poly(ethoxy)nonylphenol. PVP is usable and available at various molecular weights in the range of from about 20,000 to about 90,000. PVP having a molecular weight of about 40,000 is preferred. Poly(ethoxy)nonylphenols are commercially available under the trade designation IGEPAL from Rhone-Poulenc (Cranbury, N.J.), with various molecular weights depending on the length of the ethoxy chain. Poly(ethoxy)nonylphenols having the formula:

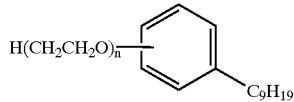

where n has an average value from about 9 to about 13 can be used. A preferred poly(ethoxy)nonylphenols is available commercially under the product name IGEPAL 630, from Rhone-Poulenc (Cranbury, N.J.)—630 is indicative of the approximate molecular weight of the compound. Other examples of suitable surfactants include polyether block copolymers, such as those available under the trade designations PLURONIC and TETRONIC, both available from BASF (Wash., N.J.), polyoxyethylene adducts of fatty alcohols, such as BRIJ surfactants available from ICI (Wilmington, Del.), and esters of fatty acids, such as stearates, oleates, and the like. Examples of such fatty acids include sorbitan monostearate, sorbitan monooleate, sorbitan sesquioleate, and the like. Examples of the alcohol portions of the fatty esters include glycerol, glucosyl and the like. Fatty esters are commercially available as surfactants under the trade designation ARLACEL C from ICI (Wilmington, Del.) Various properties of the surfactant, such as for example, chain length, functional groups, and hydrophobic regions, can affect the size of the pheromone droplets formed within the microbeads. For example, use of PVP (having a molecular weight of 40,000) tend to result in production of larger sized pheromone droplets than use of poly(ethoxy)nonylphenols (IGEPAL 630).

Ionic surfactants can alternatively be used in the processes of the invention. Examples of suitable ionic surfactants partially neutralized salts of polyacrylic acids such as sodium or potassium polyacrylate or sodium or potassium polymethacrylate.

The microencapsulated pheromone entrained in the microbeads of the invention are released gradually over time. This is a variant of the meachanism that could occur with conventional microencapsulated materials that do not have a hydrophilic matrix to cushion and protect the pheromone, since an unprotected microcapsule could potentially release the pheromone nearly all at one time, for example at the time of shell rupture. Pheromone release from the microbeads of the invention is preferably and advantageously controllable by controlling the humidity (and dryness) of the environment in which the microbeads are located.

While not being bound by this theory, it is believed that one mechanism of release of the pheromone involves water evaporation from the gel microbead followed by the diffusion of pheromone through the microcapsule shell and then through the hydrophilic microbead. Release (diffusion) by this mechanism could result in a delayed release of the pheromone. In another theorized mechanism, the pheromone becomes entrained in the water from the microbead, and as the water evaporates, the pheromone releases into the atmosphere.

In preferred applications, these hydrogel microbeads would be sprayed followed by water evaporation within the gel. As the hydrogel bead dehydrates, the microbead shrinks in size and releases its pheromone with time. The degree of shrinkage of the microbead from its original size, depending on the components used in the formulation. Preferably, the microbeads shrink about 10% to about 90% from its original size, more preferably from about 40% to about 80%, and most preferably from about 50% to about 70%.

Advantageously, the microbead, upon re-exposure to humidity, can swell and rehydrate itself by absorbing water. Re-exposure to humidity can be performed in various ways. For example, the microbeads' surfaces can be contacted directly with water or other aqueous solutions. In agricultural applications where pheromones are used, a farmer or caretaker can irrigate the plants and foliage to re-hydrate the hydrogel microbeads. Alternatively, the humidity of the environment or ambient air in which the microbeads are located in can be increased by entraining air droplets in the air. Thus, the microbeads can be "re-activated" by re-hydration, thereby selectively controlling the release times of the pheromone.

The microbeads of the invention can be delivered to an intended substrate by various methods. Pheromone delivery using microbeads depends on various factors, such as for example, the size of release coverage desired. For small concentrated areas, the microbeads can be impregnated into hollow fibres, plastic laminate flakes or twist-ties and then physically attaching the fibres or ties to plants to be protected from insect infestation. For larger areas, spraying (aerially or by backpack) may be the better option.

All patents cited in this specficiation are hereby incorporated by reference.

The following examples are for illustration purposes only and are not meant to limit the scope of the invention. Unless otherwise specified, all parts and percentages are by weight.

EXAMPLES

Comparative Example 1

Preparation of the Coacervate Microcapsule

A 100 mL of 10% (by weight) gelatin Bloom 300 solution in water, obtained from Fisher Scientific, New Jersey, was charged to a 1 liter baffled jacketed reactor fitted with a turbine impeller. The solution was mixed at 1000 rpm for 10 minutes at 50° C. 100 g of oil phase Z-11 tetradecenyl acetate obtained from Shin-Etsu, Japan was emulsified in the jacketed solution at 50° C. for 5 minutes. A 90 mL of 11% (by weight) Gum Acacia solution obtained from Fisher Scientific, New Jersey was added to the emulsion at 50° C. and mixed for 2 minutes. 1000 mL of water, preheated to 50° C. was then introduced to the mixture. The pH was lowered to about 4.4 using a 10% sodium carbonate solution. The temperature of the mixture was then lowered to between 15 and 25° C. The mixture was kept at pH of about 4.4 and temperature of between 15 and 25° C. for about 1 hour while mixing constantly at 850 rpm. About 2.6 g of Glutaraldehyde solution obtainable from Aldrich Chemical of Milwaukee, Wis., was added to the mixture with continued mixing overnight. The coacervate microcapsule formed had a mean diameter of about 20 microns.

Example 2

Preparation of Uncrosslinked Coacervate Microcapsule

A 100 mL of 10% (by weight) gelatin Bloom 275 solution in water, obtained from Aldrich Chemical of Milwaukee, Wis., was charged to a 1 liter baffled jacketed reactor fitted with a turbine impeller. The solution was mixed at 1000 rpm for 10 minutes at 50° C. 100 g of oil phase containing a 50% (by weight) blend of dodecanol, obtained from Aldrich Chemical of Milwaukee, Wis. and Mygliol 812N obtained from Condea Vista of Houston, Tex., at 50° C. was emulsified in the jacketed solution for 5 minutes. A 90 mL of 11%

(by weight) Gum Acacia solution obtained from Fisher Scientific, New Jersey, was added to the emulsion at 50° C. and mixed for 2 minutes. 1000 mL of water, preheated to 50° C. was then introduced to the mixture. The pH was lowered to about 4.4 using a 10% sodium carbonate solution. The temperature of the mixture was then lowered to between 15 and 25° C. The mixture was kept at pH of about 4.4 and temperature of between 15 and 25° C. for about 1 hour while mixing constantly at 850 rpm.

Comparative Example 3

Hydrogel Microbeads

A sodium alginate solution was initially prepared by dissolving a preweighed amount of alginate into a known volume of distilled water. The solution was mixed thoroughly to solubilize the polymer and was deaerated for removal of entrained air bubbles. In a separate 250 ml vessel, a composition of about 25% coacervate microcapsule from Example 1 above, and 2% polysaccharide solution obtained from Sigma Chemical of St. Louis, Mo., was mixed with the sodium alginate solution, creating a suspension. The suspension was thoroughly mixed at a speed of about 300 rpm using a marine type impeller (3 cm diameter). The microcapsule suspension was then atomized into fine particle droplets using a coaxial air nozzle sprayer into a calcium chloride bath (50 mM concentration). The size of the particles was determined by the settings on the atomizing device. The hydrogel microbeads produced ranged in sizes with a mean diameter of about 125 microns. These beads were then filtered and resuspended in a solution of 50 mL calcium chloride obtained from Aldrich Chemical of Milwaukee, Wis., and 0.4% xanthan gum obtained from Kelco, N.J.

Example 4

Hydrogel Microbeads Without Crosslinking

A sodium alginate solution was initially prepared by dissolving a preweighed amount of alginate into a known volume of distilled water. The solution was mixed thoroughly to solubilize the polymer and was deaerated for removal of entrained air bubbles. In a separate 250 mL vessel, a composition of about 25% coacervate microcapsule from Example 2 above, and 2% polysaccharide solution obtained from Sigma Chemical of St. Louis, Mo., was mixed with the sodium alginate solution, creating a suspension. The suspension was thoroughly mixed at a speed of about 300 rpm using a marine type impeller (3 cm diameter). The microcapsule suspension was then atomized into fine particle droplets using a coaxial air nozzle sprayer into a calcium chloride bath (50 mM concentration). The size of the particles was determined by the settings on the atomizing device. The hydrogel microbeads produced ranged in sizes with a mean diameter of about 125 microns. These beads were then filtered and resuspended in a solution of 50 mL calcium chloride obtained from Aldrich Chemical of Milwaukee, Wis., and 0.4% xanthan gum obtained from Kelco, N.J.

What is claimed:

1. A method of encapsulating a pheromone, comprising:
   a) providing a solution comprising a first polymer capable of forming a microcapsule by complex coacervation; a pheromone; and a second polymer, said second polymer being capable of forming a microcapsule by complex coacervation with the composition comprising the first polymer;
   b) establishing a microcapsule having a coacervation shell without chemical crosslinking of said shell;
   c) adding a third polymer, said third polymer being suitable to form a hydrogel microbead, in an amount effective to form a microcapsule containing composition; and
   d) spraying the microcapsule containing composition into a coordination solution, thereby providing stable hydrogel microbeads comprising microcapsules having a coacervation shell without chemical crosslinking.

2. The method of claim 1, wherein the third polymer of step c) is added before the microcapsule of step b) is established.

3. The method of claim 1, wherein the pheromone is a blend of active ingredients preselected for a particular insect pest.

4. The method of claim 1, wherein the hydrogel microbead comprises a natural occurring polymer.

5. The method of claim 1, wherein the first polymer is cationic.

6. The method of claim 1, wherein the second polymer is anionic.

7. The method of claim 1, wherein the third polymer is anionic.

8. Hydrogel microbeads made by the process of claim 1.

9. The microbead of claim 8, wherein the hydrogel microbead is coated with adhesive.

10. A pheromone containing hydrogel microbead comprising microcapsules, said microcapsules further comprising pheromones encapsulated within a coacervate shell that has not been crosslinked with aldehyde, ketone, or acid, said microcapsule being entrained within a hydrogel complex.

11. The pheromone containing hydrogel microbead of claim 10, wherein the pheromone is preselected for a particular insect pest.

12. The pheromone containing hydrogel microbead of claim 10, wherein the hydrogel microbead includes alginates.

13. The pheromone containing hydrogel microbead of claim 10, wherein the hydrogel microbead is coated with adhesive.

14. A method of retaining and delivering pheromone comprising:
   a) providing a solution comprising a first polymer capable of forming a microcapsule by complex coacervation; a pheromone; and a second polymer, said second polymer being capable of forming a microcapsule by complex coacervation with the composition comprising the first polymer;
   b) establishing a microcapsule having a coacervation shell without chemical crosslinking of said shell;
   c) adding a third polymer, said third polymer being suitable to form a hydrogel microbead, in an amount to effective form a microcapsule containing composition;
   d) spraying the microcapsule containing composition into a coordination solution, thereby providing stable hydrogel microbeads, comprising microcapsules having a coacervation shell without chemical crosslinking; and
   e) delivering said hydrogel microbeads onto a substrate in an intended environment.

15. The method of claim 14, further comprising the steps of:
   f) exposing the hydrogel microbeads to humidity; and
   g) allowing the hydrogel microbeads to rehydrate.

16. The method of claim 14, wherein the third polymer of step c) is added before the microcapsule of step b) is established.

* * * * *